United States Patent [19]

Edman et al.

[11] Patent Number: 4,820,642

[45] Date of Patent: Apr. 11, 1989

[54] AMPLIFIED EXPRESSION VECTOR

[75] Inventors: Jeffrey C. Edman, Davis; William J. Rutter, San Francisco; Robert A. Hallewell, San Francisco; Pablo D. T. Valenzuela, San Francisco; Howard M. Goodman, San Francisco, all of Calif.

[73] Assignee: The Regents of the University of California, Berkeley, Calif.

[21] Appl. No.: 481,879

[22] Filed: Apr. 4, 1983

[51] Int. Cl.$^4$ .................... C12N 1/20; C12N 15/00; C12N 1/00; C12P 21/00; C07H 21/04

[52] U.S. Cl. .................... 435/252.33; 435/68; 435/172.1; 435/172.3; 435/243; 435/320; 536/27; 935/29; 935/41; 935/72; 935/73

[58] Field of Search .................... 435/172.3, 253, 68, 435/70, 91, 849, 317; 935/11, 12, 40, 47, 48; 536/27

[56] References Cited

U.S. PATENT DOCUMENTS

| | | | |
|---|---|---|---|
| 4,237,224 | 12/1980 | Cohen et al. | 435/68 |
| 4,411,994 | 10/1983 | Gilbert et al. | 435/71 |
| 4,415,491 | 11/1979 | Vyas | 530/327 |
| 4,418,149 | 11/1983 | Ptashne et al. | 425/253 |
| 4,428,941 | 1/1984 | Galibert et al. | 424/177 |
| 4,431,739 | 2/1984 | Riggs | 435/253 |

FOREIGN PATENT DOCUMENTS

| | | | |
|---|---|---|---|
| 0009930 | 4/1980 | European Pat. Off. | 435/172.3 |
| 0013828 | 6/1980 | European Pat. Off. | |
| 0020251 | 10/1980 | European Pat. Off. | |
| 0068719 | 1/1983 | European Pat. Off. | 435/172.3 |
| 0073656 | 3/1983 | European Pat. Off. | 435/172.3 |
| 2270892 | 12/1975 | France | |
| 2034323 | 6/1980 | United Kingdom | 935/12 |
| 2070621 | 9/1981 | United Kingdom | 435/172.3 |

OTHER PUBLICATIONS

Fritsch et al., "Clonage du Genome du Virus de l'Hepatite B Dans *Escherichia coil*", C. R. Acad. Sc. Paris, Series D, 287: 1453. (1978).

Galibert et al., "Nucleotide Sequence of the Hepatitis B Virus Genome (Subtype ayw) Cloned in E. coli", *Nature* 281: 646 (1979).

Burrell et al., "Expression in *Escherichia coli* of Hepatitis B Virus DNA Sequences Cloned in Plasmid pBR322", *Nature* 279: 43 (1979).

Pasek et al., "Hepatits B Virus Genes and Their Expression in *E. coli*", *Nature* 282: 575 (1979).

Stauffer et al., "In Vivo Cloning of DNA Regions Carrying Mutations Linked to Selectable Genes: Applications to Mutations in the Regulatory Region of the *Escherichia coli* Tryptophan Operon", *Plasmid* 2: 498 (1979).

Hallewell et al., "Plasmid Vectors Containing Tryptophan Operon Promotor Suitable for Efficient Regulated Expression of Foreign Genes", *Gene* 9: 27 (1980).

Mackie et al., "Tandem Promoters in the Gene for Ribosomal Protein S20 ", *J. Biol. Chem.* 258: 7840 (1983).

Valenzuela et al., "Nucleotide Sequence of the Gene Coding for the Major Protein of Hepatitis B Virus Surface Antigen", *Nature* 280: 815 (1979 ).

Fritsch et al.; C. R. Acad. Sci. Paris 287 (Series D): 1453 (1978).

Galibert et al.; Nature 281: 646 (1979).

Burrell et al.; Nature 279: 43 (1979).

Stauffer et al.; Plasmid 2: 498 (1979).

Hallewell et al.; Gene 9: 27 (1980).

(List continued on next page.)

*Primary Examiner*—James Marinell
*Attorney, Agent, or Firm*—Ciotti & Murashige, Irell & Manella

[57] ABSTRACT

A DNA expression vector which contains the trp promoter is described. The expression vector provides for the overproduction of β-lactamase. Insertion of a gene or cDNA into the β-lactamase gene of the expression vector results in the over-production of a fusion protein comprising a part of the β-lactamase as the N-terminal end and the protein coded for by the inserted DNA as the C-terminal end. Using the expression vector described herein, it is possible to obtain large amounts of the fusion protein. A fusion protein containing the surface antigen of Hepatitis B virus and a vaccine containing this fusion protein are also described.

6 Claims, 3 Drawing Sheets

OTHER PUBLICATIONS

Valenzuela et al.; Nature 280: 815 (1979).

Alwine, J. C., et al., "Method of Detection of Specific RNAs in Agarose Gels by Transfer to Diazobenzyloxymethyl-Paper and Hybridization with DNA Probes", *Proc. Natl. Acad. Sci.* 74, 5350 (1977).

Beggs, J. D., "Abnormal Expression of Chromosomal Rabbit Betaglobin Gene in *Saccharomyces cerevisiae*", *Nature*, vol. 283, 835 (1980).

Blumberg, B. S., "Australian Antigen and the Biology of Hepatitis B", *Science*, vol. 197, 17 (1977).

Bolivar, F., "Construction and Characterization of New Clonging Vehicles: III Derivatives of Plasmid pBR322 . . . "]*Gene*, 4:121 (1977).

Bolivar, F., "Construction and Characterization of New Cloning Vehicles: II A Multipurpose Cloning System", *Gene*, 4:95, (1977).

Boyer, H. W. and Rolland-Dussiox, "A Complementation Analysis of the Restriction and Modification of DNA in *Escherichia coli*, *Journal of Molecular Biology*,'-'vol. 41, 459-472 (1969).

Charnay, P., et al., "Localization on the Viral Genome and Nucleotide Sequence of the Gene Coding for the Two Major Polypeptides of the Hepatitis B Surface Antigen (HBsAg)", *Nucleic Acids Research*, vol. 7, 2 (1979).

Christman, J. K., "Amplification of Expression of Hepatitis B Surface Antigen in 3T3 Cells Contransfected with a Dominant-Acting Gene and Cloned Viral DNA", *Proc. Natl. Acad. Sci.-USA*, vol. 79, 1815 (1982).

Crick, F. H. C., "Split Genes and RNA Splicing", *Science*, vol. 204, 264 (1979).

Datta, N., "The Purification and Properties of the Penicillinase Whose Synthesis is Mediated by an R-Factor in *E. coli*", *Chem. Abstracts*, 64:8558h (1966).

DuBois, M. -F., et al., "Excretion of Hepatitis B Surface Antigen Particles from Mouse Cells Transformed with Cloned Viral DNA", *Proc. Natl. Acad. Sci.*, vol. 77, 4549 (1980).

Edman, et al., "Integration of Hepatitis B Virus Sequences and Their Expression in a Human Hepatoma Cell", *Nature* (London) vol. 286 (5772), 535–(1980).

Enger-Valk, B. E., et al., "Construction of New Cloning Vehicles with Genes for Tryptophan Operon of *E. coli.* as Genetic Markers", Abstract, *Chem. Abstr.* 92:194275m (1980).

Guarente, L., et al., "A Technique for Expressing Eukaryotic Genes in Bacteria", *Science*, 209, 1428 (1980).

Itakura, K., et al., "Expression in *Escherichia coli* of a Chemically Synthesized Gene for the Hormone Somatostatin", *Science*, vol. 198, 1056 (1977).

Macnab, G. M., et al., "Hepatitis B Surface Antigen Produced by a Human Hepatoma Cell Line", *Journal of Cancer*, vol. 34, 509 (1976).

Maxam, A. M., "A New Method for Sequencing DNA", *Proc. Natl. Acad. Sci.-USA*, vol. 74, 560 (1977).

Mercereau-Puijalon. O., et al., "Synthesis of an Ovalbumin-Like Protein by *Escherichia coli* K12 Harbouring a Recombinant Plasmid", *Nature*, vol. 275, 505 (1978).

O'Farrell, P. H., et al., "Regulated Expression by Read-Through Translation from A Plasmid-Encoded Beta-Galactosidase" *J. Bact.*, 134, 645 (May 1978).

Shih, J. W., et al., "Proteins of Hepatitis B Surface Antigen", *Journal of Virology*, 21, 347 (Jan. 1977).

Shih, J. W., et al., "Proteins of Hepatitis B Surface Antigen: Amino Acid Compositions of the Major Polypeptides", *Journal of Virology*, 21, 1219 (Mar. 1977).

Silhavy, T. J., et al., "Conversion of Beta-Glactosidase to a Membrane-Bound State by Gene Fusion", *Proc. Natl. Acad. Sci.*, U.S.A. 73, 3423 (Oct. 1976).

Skelly, J., et al., "Hepatitis B Polypeptide Vaccine Preparation in Micelle Form", *Nature*, vol. 290, 51 (1981).

Southern, E. M., "Detection of Specific Sequences Among DNA Fragments Separated by Gel Electrophoresis", *Journal of Molecular Biology*, vol. 98, 503 (1975).

Villa-Komaroff, L., et al., "A Bacterial Clone Synthesizing Proinsulin", Proc. Natl. Acad. Sci., vol. 75, 3727 (1978).

Helling et al. "The Molecular Cloning of Genes", in *Genetic Engineering*, Chakrabarty (ed.), CRC Press, West Palm Beach, Fla., 1978, pp. 1–30.

Charnay, P., et al, "Brosynthesis of Hepatits B Virus Surface Antigen in *Escherichia coli*", *Nature* 286, 893 (1980).

Edman, J. C., et al., "Synthesis of Hepatitis B Surface and Core Antigens in *E. coli*", *Nature* 291, 503 (1981).

Pasek, M., et al., "Hepatitis B Virus Genes and their Expression in *E. coli*" *Nature* 282, 575 (1979.

Peterson, D. L. et al., "Partial Amino Acid Sequence of Two Major Component Polypeptides of Hepatitis B Surface Antigen", Proc. Natl. Acad. Sci. U.S.A., 74, 1530 (1977).

Peterson, D. L. et al. "Characterization of Polypeptides of HBsAg for the Proposed 'UC Vaccine' for Hepatitis B", in *Viral Hepatitis: A Contemporary Assessment Etiology, Epidemiology, Pathogenesis and Prevention*, Vyas, GN et al. eds, Franklin Negt. Press, Philadelphia, 1978, pp. 569-573.

4,820,642

AMPLIFIED EXPRESSION VECTOR

This is a continuation of application Ser. No. 213,880, filed Dec. 8, 1980, now abandoned.

BACKGROUND OF THE INVENTION

One of the goals of recombinant DNA technology is to obtain efficient expression of the cloned DNA. It is desirable to obtain the expression product in as high yields as possible. Several possible techniques for expression are available as options, and may include (a) modification of the coding sequences to provide an exact desired translational starting point; (b) selection or construction of an optimal expression vector; (c) post-translational processing, either by exploiting in vivo processing activity of the host or by in vitro chemical means; and (d) direct expression.

Cloned DNA can be expressed as a fusion protein which contains the protein coded for by the cloned DNA as the C-terminal end. The protein coded for by the foreign gene or cDNA can be expressed as a fusion protein by insertion of the foreign gene or cDNA into appropriate sites within expressed operons (expression vectors) including, for example, the Pst I site in the $\beta$-lactamase gene of pBR322 (Villa-Komaroff, L., et al, *Proc. Nat. Acad. Sci. USA*, 75, 3727 (1978) and Seeburg, P., et al, *Nature*, 274, 795 (1978)), the EcoRI site of pBR322 carrying the lac control region and coding sequence for $\beta$-galactosidase (Itakura, K., et al, *Science*, 198, 1056 (1977)) or the HindIII site of the trpD gene of plasmid ptrpED50 (Martial, J., et al, *Science*, 205, 602 (1979)). Modifications of sequence length, if needed, by one or two nucleotides in order to achieve correct reading frame phase are well known in the art.

Cloned DNA can be expressed directly under certain circumstances. Chang, A.C.Y., et al, *Proc. Nat. Acad. Sci. USA*, 77, 1442 (1980) have reported that they obtained direct expression of mouse dihydrofolate reductase when the coding sequence therefor has been dC-tailed and inserted into the dG-tailed, Pst I site of pBR322. A second technique for direct expression involves replacing the coding segment normally transcribed and translated by a bacterial control region, which includes a promoter and ribosomal binding site, with any desired coding sequence. Application Ser. 213,879, filed Dec. 8, 1980 (and its continuation; Ser. No. 518,613, filed July 29, 1983), incorporated herein by reference describes the synthesis of a direct expression vector containing the control region of the trp operon.

The trp operon has proved useful for the expression of a fusion protein or for direct expression. Several expression vectors containing the trp operon have been prepared for use in synthesizing fusion proteins. Hallewell, R. A. and Emtage, R. A., *Gene*, 9, 27 (1980) describe the preparation of an expression vector, ptrpED5-1, containing the promoter, operator, leader, attenuator, trp E gene and 15% of the trp D gene sequences. This expression vector has been utilized to produce a fusion protein containing part of the trp D protein and human growth hormone (Martial, J., et al, supra). Tacon, W., et al, *Molec. Gen. Genet.*, 177, 427 (1980) describe the preparation of expression vectors pWT 111, pWT 121 and pWT 131. These expression vectors are derived from ptrpED5-1 by digestion with HinfI to remove the DNA sequences of the trp D gene and all but 21 deoxyribonucleotides of the trp E gene.

In each of the above expression methods utilizing the trp operon, maximum expression is not obtainable. The trp operon contains two transcriptional control points. The primary control point is the promoter/operator region. Transcription of the operon is regulated by trp repressor molecules binding at this site and repressing the operon. The addition of $3\beta$ indolylacrylic acid induces the trp operon approximately 50-fold. A secondary control point involves the leader and attenuator sequence of the operon. This sequence regulates transcription of the trp operon by approximately 10-fold, by terminating transcription at this point (Bertrand, K., et al, *Science*, 189, 22 (1975)). When trp tRNA is limiting, translation pauses at these two codons and transcription continues past the attenuator. However, when trp tRNA is abundant, translation continues and transcription terminates at the attenuator, yielding a 140 bp transcript corresponding to the leader region.

While it is possible to induce the trp operon 50-fold with $3\mu$-indolylacrylic acid, it is not possible to maximize transcription and hence expression when the trp operon expression vector contains the attenuator sequence. Application Ser. No. 213,879 (and its continuation, supra) describes a direct expression vector (ptrpL1) which is derived from the trp operon and lacks the attenuator sequence. Although this expression vector is suitable for the direct expression of many proteins, it has been discovered that it is not suitable for the direct expression of all proteins. For example, applicants discovered that insertion of the hepatitis B surface antigen (HBsAg) gene into the Cla I site of ptrpL1 did not result in the production of HBsAg.

While it is possible to synthesize fusion proteins containing a part of the $\beta$-lactamase protein by the prior art methods, it has often not been possible to obtain expression of some fusion proteins in a significant amount to make the prior art methods practical. Applicants have discovered that the location of the trp promoter upstream from the $\beta$-lactamase gene in ptrpL1 results in the overproduction of $\beta$-lactamase when the trp promoter is induced by $3\beta$-indolylacrylic acid. Applicants further discovered that a fusion protein is also overproduced when foreign DNA is inserted into the $\beta$-lactamase gene. Applicants hypothesize that the trp promoter is overriding the $\beta$-lactamase promoter to cause the overproduction of the $\beta$-lactamase or the fusion protein.

SUMMARY OF THE INVENTION

The present invention discloses a DNA expression vector which contains the trp promoter. Foreign DNA is inserted into the $\beta$-lactamase gene of the expression vector. The expression vector provides for the production of a large amount of a fusion protein comprising a portion of the $\beta$-lactamase as the N-terminal and the protein coded for by the inserted DNA as the C-terminal end. Since the expression vector provides for the amplification of the amount of fusion protein produced, it is termed an amplification expression vector. The procedure of preparing the amplification expression vector is also described.

Specifically, an expression vector containing the HBsAg gene is described. A method of forming a fusion protein containing HBsAg is described as well as a vaccine prepared from the fusion protein.

DETAILED DESCRIPTION OF THE INVENTION

The synthesis of the plasmid ptrpL1 is described in application Ser. No. 213,879 (and its continuation, supra), incorporated herein by reference. Nevertheless, the basic method is also set forth herein for the sake of completeness.

Throughout this description the following nomenclature is utilized. A plasmid containing the trp operon is designated ptrp. The amount of the trp operon included in the plasmid is the next part of the designation. Thus, "E" refers to the sequence through part of the E gene, "ED" refers to the sequence through part of the D gene; and "L" refers to the sequence through the leader ribosomal binding site. The first number which appears after these "E", "ED" or "L" designations identifies the colony from which the plasmid was isolated. The second number, −1, 0 or +1, when it appears, refers to the reading frame at the insertion site. The "O" designation means that the reading frame is in phase with the start codon.

The 487 base pair HinfI fragment of the trp operon (Lee, F., et al, $J.$ $Mol.$ $Biol.,$ 121, 193 (1978)) is obtained by digesting plasmid ptrpED5-1 with HinfI restriction endonuclease. The protruding 5' ends are filled in with the use of the Klenow fragment of DNA polymerase I and the appropriate deoxynucleotides. A linker nucleotide sequence containing the restriction sequence for HindIII endonuclease is blunt-end ligated to the filled-in HinfI fragment by the procedure of Ullrich, et al., $Science$ 196, 1313 (1977). Insertion of this fragment into pBR322 is accomplished by following the procedure of Ullrich, A., et al, $Science,$ 196, 1313 (1977). This mixture is then used to transform a suitable host, such as $E.$ $coli$ 1776, RR1, HB101 or other bacteria as described by Seeburg, P.H., et al, $Nature,$ 270, 496 (1977) and colonies are selected on ampicillin. A recombinant clone with the trp promoter directed towards the β-lactamase gene is obtained by screening DNA miniscreens for a 200 base pair HpaI-EcoRI fragment. This procedure involves isolating and analyzing the DNA from colonies of transformed bacteria. This plasmid is designated as ptrpE2-1.

Figure 1:
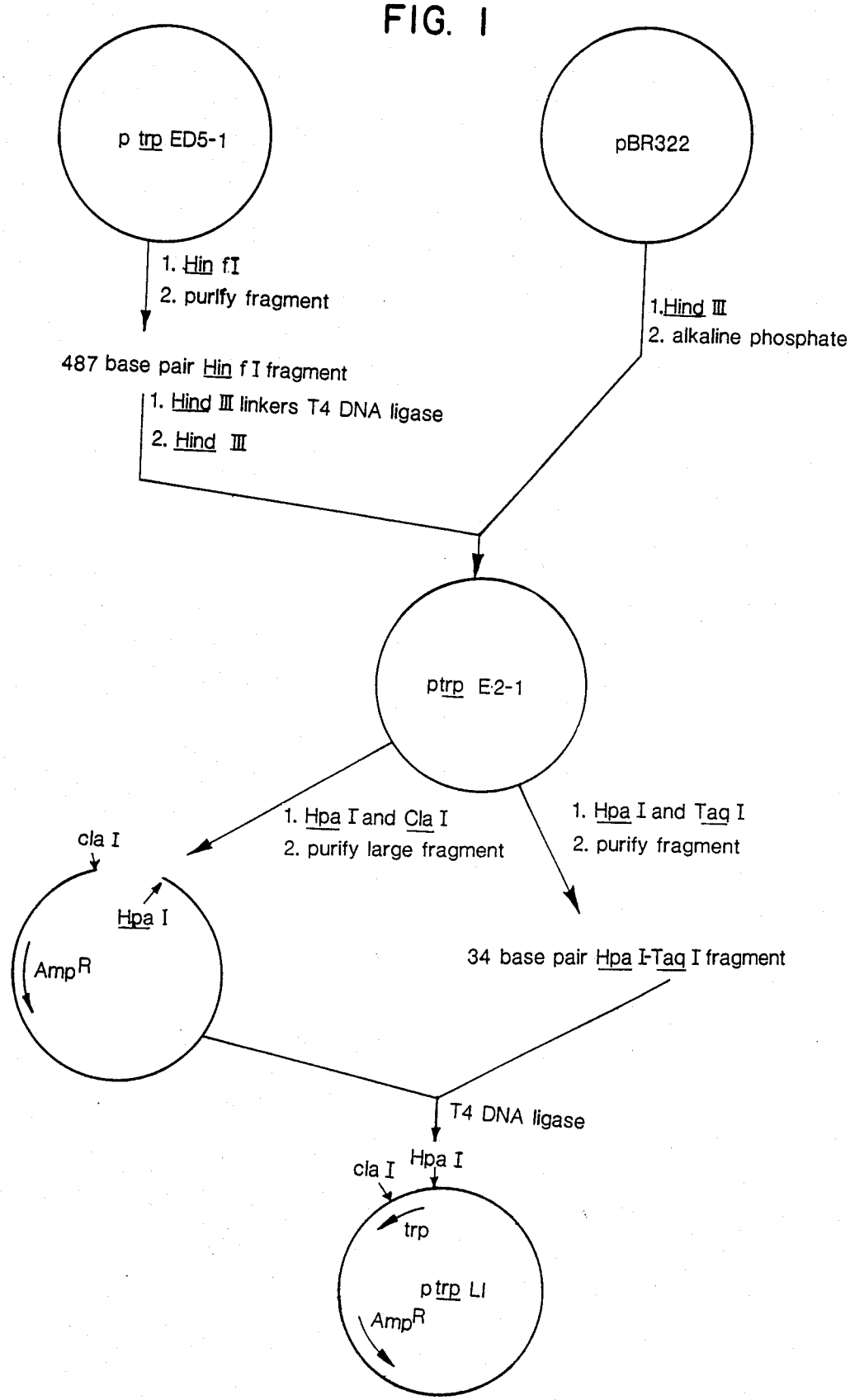
FIG. 1 Construction of ptrpL1

The plasmid ptrpE2-1 is digested with a mixture of Hpa I and Cla I restriction endonucleases to remove approximately 180 base pairs. This removes part of the promoter, the operator, leader, attenuator and E gene sequences. A second portion of plasmid ptrpE2-1 is digested with a mixture of Hpa I and Taq I restriction endonucleases to remove a Hpa I—Taq I fragment comprising 34 base pairs. This sequence contains part of the promoter, the operator and leader ribosomal binding site. This fragment is isolated and purified by preparative gel electrophoresis. The Hpa I—Taq I fragment is ligated with the Hpa I—Cla I restricted ptrpE2-1 using a 3-fold molar excess of said fragment and T4 DNA ligase, essentially as described by Ullrich et al, supra. The resulting plasmid is used to transform a suitable host, such as $E.$ $coli$ X1776, RR1, HB101 or other bacteria and colonies are selected on ampicillin. A recombinant clone is obtained by screening DNA miniscreens for a 34 base pair Hpa I—Cla I fragment. This plasmid is designated ptrpL1. FIG. 1 illustrates the method of forming ptrpL1. The trp promoter is located approximately 200 base pairs from the β-lactamase gene.

In order to obtain a fusion protein comprising a portion of β-lactamase and the desired protein, the foreign DNA coding for the desired protein is inserted into the β-lactamase gene. One method of performing this insertion is to utilize the Pst I site within the β-lactamase gene of ptrpL1. The plasmid ptrpL1 is digested with Pst I and is dG-tailed using dGTP and terminal transferase by the procedure described by Roychoudhury, R., et al, $Nucl.$ $Acids$ $Res.,$ 3, 863 (1976). The desired foreign DNA is isolated using conventional techniques and is dC-tailed by the same procedure, using dCTP in place of dGTP. The dG-tailed, Pst I digested ptrpL1 and the dC-tailed foreign DNA are hybridized by following the procedure described by Chang, A.C.Y., et al, $Nature,$ 275, 617 (1978). Modifications of sequence length by one or two nucleotides prior to dC-tailing in order to achieve correct reading frame phase are well known in the art. Insertions at the Pst I site, with the aid of the tailing procedure, occur in correct phase and reading frame with a probability of 1/6. Host bacteria, such as $E.$ $coli$ X1776, RR1, HB101 or other bacteria are transformed by the amplified expression vector containing the foreign DNA. Transformants are selected for sensitivity to ampicillin and grown under conditions suitable for expression of the foreign DNA. Expression of the foreign DNA can be seen by new translational products not seen in non-transformed bacteria or uninduced bacteria.

Other transfer vectors suitable for amplified expression can be prepared in a similar manner. The requirements for preparing an amplified expression vector are: (1) the presence of a procaryotic gene into which a foreign deoxyribonucleotide sequence can be inserted; (2) the promoter of this procaryotic gene; and (3) a second promoter located upstream from the procaryotic gene promoter which overrides the procaryotic gene promoter, thus resulting in overproduction of the procaryotic gene product or fusion protein. The "second promoter" is obtained in any suitable manner. For example, it can be obtained as described herein. Alternatively, it can be obtained by removing the promoter and surrounding sequence with suitable restriction endonucleases. As much of the surrounding sequence as necessary is removed in order to provide the promoter in the appropriate form. This removal can be accomplished by any of the methods set forth in application Ser. No. 599,464, filed Apr. 12, 1984; which is a continuation of application Ser. No. 403,405, filed July 30, 1982; which is a continuation of application Ser. No. 125,878, filed Feb. 29, 1980, incorporated herein by reference. This "second promoter" is then inserted at a point upstream from the promoter of a procaryotic gene in a transfer vector using conventional techniques. The resulting transfer vector is then used to transform a microorganism. The transformed microorganism is cultured and protein products analyzed to determine if there is an overproduction of the procaryotic gene. Those transfer vectors causing an overproduction of the procaryotic gene are then utilized for the amplified expression of a foreign DNA sequence. A foreign DNA sequence is inserted into the procaryotic gene of these transfer vectors using conventional techniques. Transformation and expression are accomplished using conventional techniques resulting in the expression of a large amount of the fusion protein.

If foreign DNA coding for a viral protein is inserted into the amplified expression vector, a fusion protein containing the viral protein is produced. If this fusion protein is capable of eliciting the formation of antibodies, vaccines containing the fusion protein are then produced using conventional techniques.

The details of the present invention will be further described by the following examples. In these examples, digestions with restriction endonucleases were carried out under conditions optimized for each enzyme. Restriction endonucleases, their nomenclature and site specificity, have been described in detail by Roberts, R., *Nucleic Acids Res.*, 8, r63-r80 (1980). Enzymes were obtained commercially (New England BioLabs, Cambridge, Mass.) and optimal conditions according to supplier's recommendations were employed unless noted otherwise. T4 DNA ligase was obtained from New England BioLabs. The use of T4 DNA ligase and suitable reaction conditions have been previously described by Valenzuela, et al, supra, and Ullrich, et al, supra. HpaII methylase was provided by Dr. K. Agarwal, University of Chicago, Chicago, Ill. Terminal deoxynucleotide transferase was obtained from Enzo Biochemicals, New York, N.Y. The use of this enzyme and suitable reaction conditions have been previously described by Roychoudhury, et al, supra. The Klenow fragment of DNA polymerase I was obtained from New England BioLabs. The use of the Klenow fragment of DNA polymerase I and suitable reaction conditions have been previously described by Klenow, H. and Hennigsen, I., *Proc. Nat. Acad. Sci. USA*, 65, 168 (1970). Synthetic linker molecules were obtained from Collaborative Research, Inc., Waltham, Mass.

EXAMPLE 1

Plasmid ptrpED5-1 was prepared as described by Hallewell and Emtage, supra. 10 μg of ptrpED5-1 was digested with HinfI and the resulting fragments made flush-ended by a 10-minute incubation at 20° C. with the Klenow fragment of DNA polymerase I in a reaction volume of 20 μl containing 1μl of the polymerase, 50 mM Tris pH 7.5, 10 mM MgCl$_2$, 500 μM each of dATP, dTTP, dCTP and dGTP and 10 mM 2-mercaptoethanol. The 500 base pair HinfI fragment containing the trp regulatory region was eluted from a 5% acrylamide gel and ethanol precipitated. The HinfI fragment was then ligated to a hundred-fold molar excess of synthetic HindIII linker molecules (d(pCCAAGCTTGG)) in a reaction volume of 30 μl containing 2 μl T4 DNA ligase, 50 mM Tris pH 7.5, 10 mM MgCl$_2$, 10 mM dithiothreitol and 1 mM rATP at 15° C. for 16 hours. The ligase is inactivated by heat treatment at 68° C. for 5 minutes. The HindIII linker treated HinfI fragment was cut with HindIII, the mixture was extracted with phenolchloroform and ethanol precipitated. Excess linker molecules and linker molecule fragments were removed from the HinfI fragment by chromatography on Sepharose™ CL 4B (Pharmacia, Inc., Uppsala, Sweden). The plasmid pBR322 was cut with HindIII, treated with alkaline phosphatase and the HinfI fragment inserted into the HindIII site by following the procedure described by Ullrich, et al, supra. Host bacteria *E. coli* RR1 were transformed by the resulting recombinant vector bearing the 487 base pair Hinf fragment and transformants were selected for resistance to ampicillin. A recombinant clone with the trp promoter directed towards the β-lactamase gene was obtained by screening DNA miniscreens for a 200 base pair Hpa I—Eco RI fragment. This plasmid was designated ptrpE2-1.

A first portion of the plasmid ptrpE2-1 was digested with a mixture of Hpa I and Taq I and a 34 base pair Hpa I—Taq I fragment was purified by polyacrylamide gel electrophoresis. A second portion of the plasmid ptrpE2-1 was digested with a mixture of Cla I and Hpa I. The Cla I—Hpa I treated ptrpE2-1, i.e., ptrpE2-1 lacking a Cla I—Hpa I fragment, was purified by polyacrylamide gel electrophoresis and then ligated to a threefold molar excess of the purified Hpa I—Taq I fragment using T4 DNA ligase following the procedure described by Ullrich, et al, supra. Host bacteria *E. coli* HB101 were transformed by the resulting recombinant vector bearing the promoter, operator and leader ribosomal binding site of the trp operon. Transformants were selected for resistance to ampicillin. A recombinant clone was obtained by screening DNA miniscreens for a 34 base pair Hpa I—Cla I fragment. This plasmid was designated ptrpL1. The plasmid was also found to contain a single Cla I site, a single HindIII site and the expected DNA sequence around the Cla I site.

EXAMPLE 2

Hepatitis B surface antigen (HBsAg) gene was inserted into ptrpL1 in order to demonstrate the amplified expression of foreign DNA. This example was conducted after it was discovered that HBsAg was not directly expressed when the gene had been inserted into the Cla I site of ptrpL1 and that β-lactamase was overproduced by ptrpL1.

A recombinant clone containing the entire hepatitis B virus DNA, as described by Valenzuela, P., et al, *Nature*, 280, 815 (1979) and Valenzuela, P., et al, *Animal Virus Genetics*, Fields, B., Janenisch, R. and Fox, C. F., Ed., Academic Press, New York, N.Y., 1980 was digested with HindIII. A 750 base pair fragment containing the coding sequence for all of HBsAg except for 22 amino acids of the N-terminal end was isolated by preparative acrylamide gel electrophoresis. The lacking 22 amino acids are believed to be the signal peptide which is normally cleaved during translation. Approximately 15 dC residues were added to the 3' ends of the fragment using terminal transferase as described by Roychoudhury, et al, supra. The plasmid ptrpL1 was digested with Pst I and approximately 15 dG residues were added to the 3' ends using terminal transferase as described by Roychoudhury, et al, supra. The dC-tailed fragment and dG-tailed, Pst I cut ptrpL1 were hybridized as described by Chang, A.C.Y., et al, *Nature*, supra. Host bacteria HB101 were transformed by the resulting recombinant vector bearing the HBsAg gene. Transformants were selected on L plates (Miller, J. H., *Experiments in Molecular Genetics*, Appendix I, Cold Spring Harbor Laboratory, Cold Spring Harbor, L.I., N.Y. (1972B)) containing 2.5 μg/ml tetracycline and tested for ampicillin resistance on plates containing 20 μg/ml ampicillin.

Figure 2:
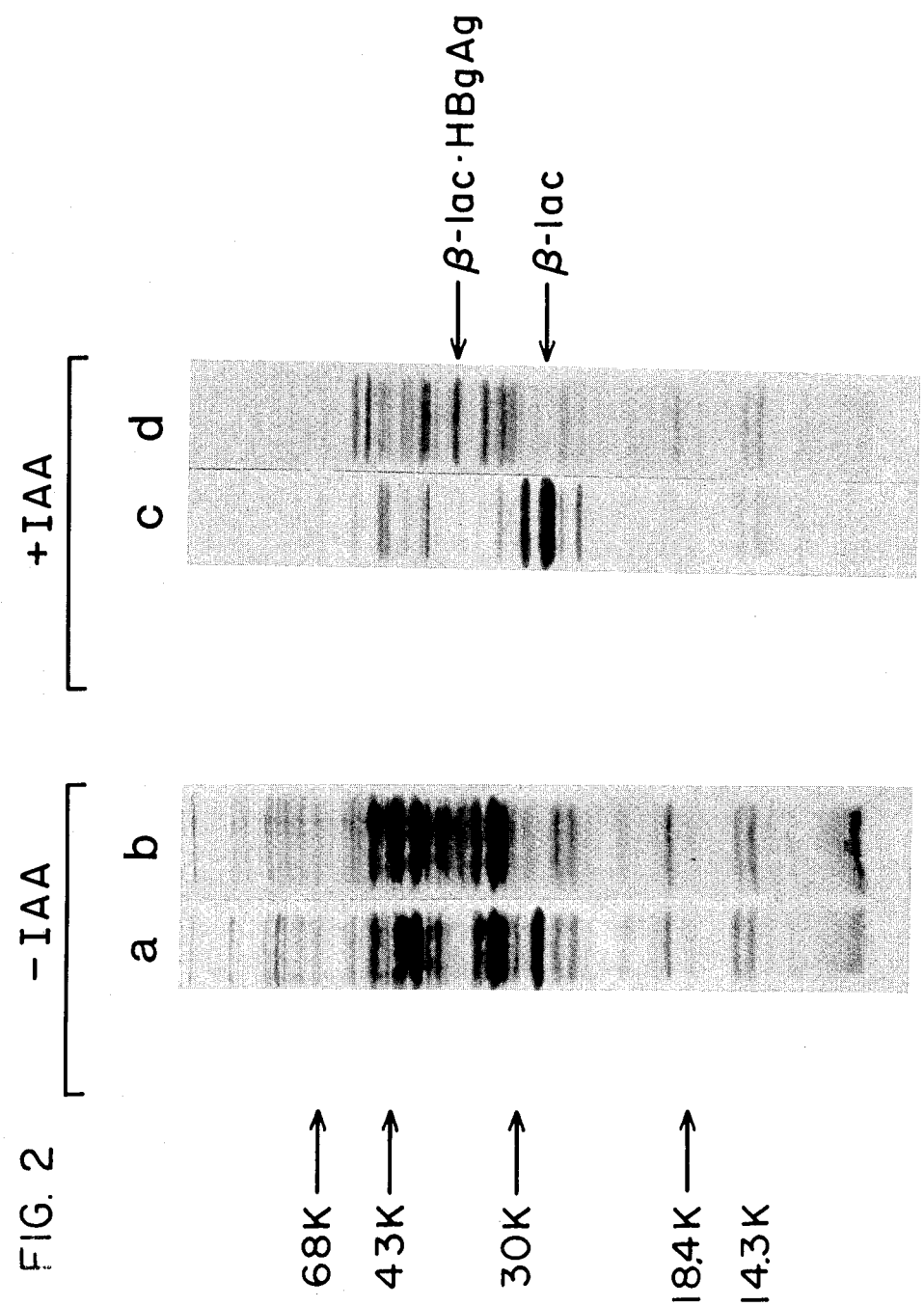
FIG. 2 Electrophoresis of protein products: lane a, ptrpL1 without 3-β-indolylacrylic acid (IAA): lane b. PSA4A without IAA; lane c, ptrpL1 induced by IAA lane d. psA4A induced by IAA.

Overnight cultures of 38 ampicillin-sensitive transformants were prepared in M9 media (Miller, J. H., supra) containing 0.25% casamino acids, 0.5% glucose and 0.01% B1. The cultures were diluted 1:10 with fresh media, grown for one hour at 30° C., 15 μg/ml of 3β-indolylacrylic acid was added, and the cultures grown for another two hours at 30° C. Cultures in which 3β-indolylacrylic acid was not added were used as the controls. The cultures were then labelled for 20 minutes at 30° C. with 10μ Ci/ml of $^{35}$S-cysteine. The protein products were electrophoresed on sodium dodecylsulfate-polyacrylamide gels and the protein bands were visualized by autoradiography. Two clones, identified as pSA4A and pSA7A, were found which produced a new protein of about 41,000 daltons—the predicted weight for a fusion protein containing β-lactamase and HBsAg. FIG. 2 illustrates the results which were obtained with pSA4A. Lanes a and b are protein samples from uninduced ptrpL1 and pSA4A, respectively. Lanes c and d are protein samples from induced ptrpL1 and pSA4A, respectively.

Figure 3:
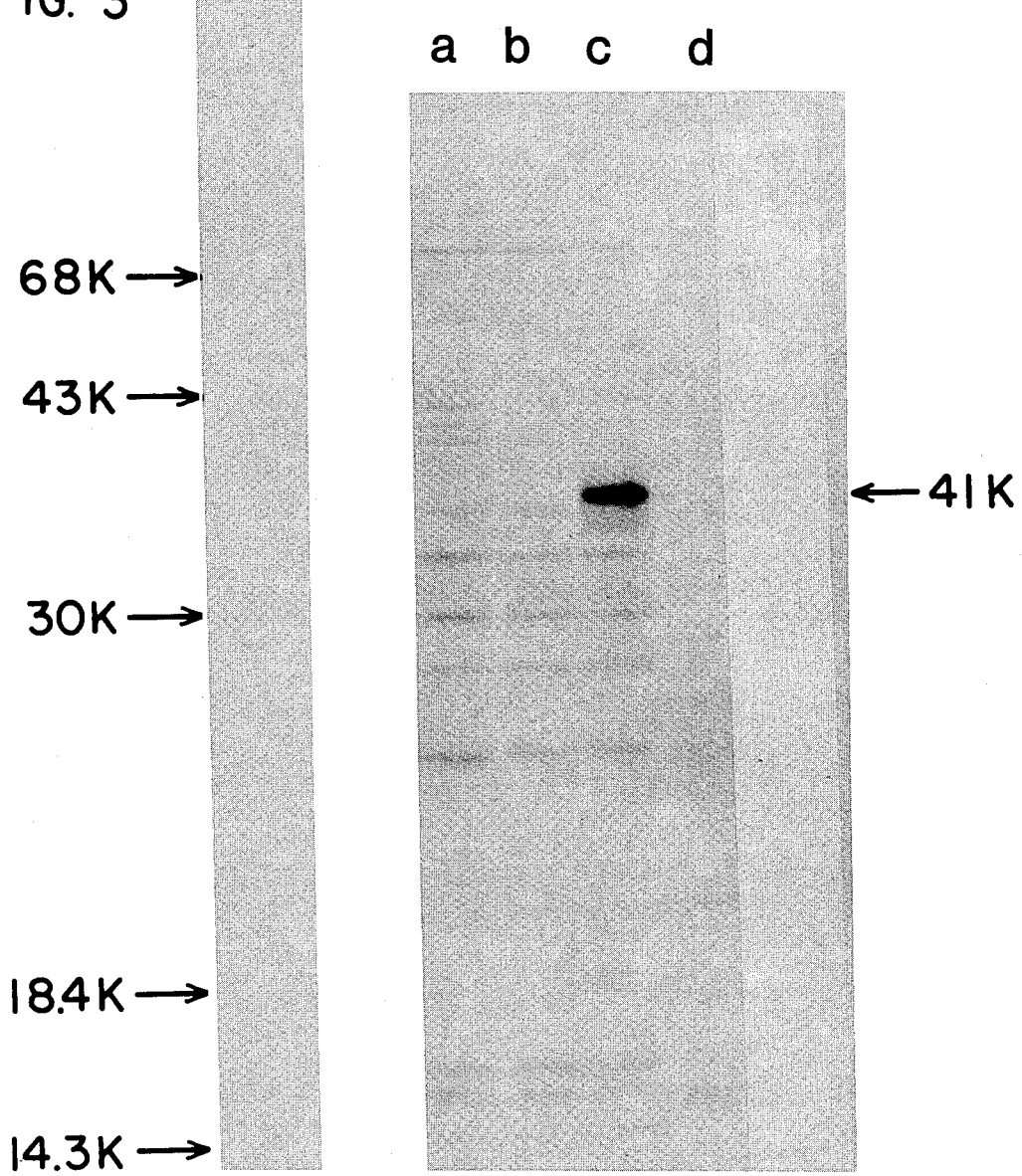
FIG. 3 Immunoprecipitation of fusion protein product: lane, pSA immunoprecipitated with normal guinea pig IgG; lane b, pSA4A plus 2 micrograms unlabelled HBsAg and guinea pig anti-HBsAg; lane c, pSA4A plus guinea pig anti-HBsAg; lane d, ptrpL1 plus anti-HBsAG.

Cells were grown and labelled with $^{35}$S-cysteine as described above. The labelled cells were collected by centrifugation and resuspended in phosphate-buffered saline containing 1 mM phenylmethylsulfonylfluoride. The cells were sonicated and proteins immunoprecipitated with anti-HBsAg serum or normal IgG as the control using the SAC technique described by Martial, J. A., et al, *Science*, 205, 602 (1979). The predominant band is the 41,000 dalton polypeptide as shown in FIG. 3. Addition of cold HBsAg inhibits the precipitation completely. Samples are: (d) ptrpL1 plus anti-HBsAg; (a) pSA4A plus normal , guinea pig IgG; (b) pSA4A plus 2 μg unlabelled HBsAg and guinea pig anti-HBsAg; and (c) pSA4A plus guinea pig anti-HBs FIGS. 2 and 3 clearly show that a fusion protein containing HBsAg is produced by transformed cells and that the trp promoter causes an overproduction of the fusion protein.

EXAMPLE 3

It was determined that the fusion protein containing HBsAg contains only one antigenic site whereas the native HBsAg contains more than one. The one antigenic site of the fusion protein is sufficient to give a binding reaction with an antibody but not not sufficient for antibody precipitation, as occurs with the native HBsAg. This binding reaction is sufficient to confer immunity.

The β-lactamase-HBsAg fusion protein is sufficiently antigenic to elicit antibodies which are cross-reactive with native HBsAg. The β-lactamase-HBsAg fusion protein expressed as described in Example 2 is purified from cell lysates using conventional techniques, including among others, gel filtration and affinity chromatography. Guinea pigs are injected subcutaneously at 9, 14 and 56 day intervals with 10 ml physiological saline or phosphate-buffered saline containing 500 μg of the purified β-lactamase-HBsAg fusion protein. The serum of the test animals is sampled at 0, 28, 56 and 84 days and assayed for antibody titre against Dane particles or HBsAg partially purified from infectious serum. The radioimmunoassay of Hollingren, F., et al, *J.Immunol.*, 107, 1099 (1971) is employed. The majority of animals exhibit antibodies cross-reactive with HBsAg 84 days after administration of the protein. Similar results are obtained upon injection of monkeys. Accordingly, the immunologically active protein oonstituent of Hepatitis B virus, expressed by a microorganism that has been transformed by a DNA transfer vector encoding HBsAg, are capable of eliciting antibodies cross-reactive with an immunologically reactive component of the virus.

The described proteins have the advantage of being available in significantly larger quantities than HBsAg obtained from Dane particles, carrier serum or prior methods of cloning HBsAg, for example, as described in application Ser. No. 771,123, filed Aug. 30, 1985; which is a continuation of Ser. No. 041,909, filed May 24, 1979. Furthermore, there is no danger of accidental infection since there is no intact virus in the β-lactamase-HBsAg expression product. By contrast, viral proteins purified from serum always pose the danger of viral contamination.

Since this fusion protein is capable of eliciting antibodies cross-reactive with native HBsAg, it therefore follows that the purified fusion protein administered in physiologically acceptable medium constitutes a vaccine for protection against infection by the hepatitis B virus.

Sixteen chimpanzees are divided into three groups. Group A (6 animals) is inoculated intravenously with 1.0 ml of B.0.B. Hepatitis B virus; Group B (4 animals) is inoculated intravenously with 1.0 ml containing 5 mg. of the purified β-lactamase—HBsAg fusion protein in physiological saline; Group C (6 animals) is the control group and receives no inoculation. All chimpanzees in Group A have evidence of clinical hepatitis B (either antigenemia, enzyme elevations and/or antibody response) within forty weeks. None of the animals in Groups B or C shows evidence of clinical hepatitis B infection over the same 40-week period. The chimpanzees of Group B are rendered immune to subsequent challenge when inoculated intravenously with 1.0 ml of B.0.B. hepatitis B virus.

While the invention has been described in connection with specific embodiments thereof, it will be understood that it is capable of further modifications. This application is intended to cover any variations, uses or adaptations of the invention following, in general, the principles of the invention and including such departures from the present disclosure as come within known and customary practice within the art to which the invention pertains.

Recombinant bacterial strain *Escherichia coli* HB101/pSA4A and recombinant plasmid pSA4A were placed on deposit in the American Type Culture Collection, 12301 Parklawn Dr., Rockville, Md. 20852, on Dec. 5, 1980, and have been assigned the ATCC Accession Numbers 31756 and 40034, respectively.

What is claimed is:

1. A hybrid plasmid useful for amplified expression of a foreign DNA sequence, comprising a β-lactamase gene having said foreign DNA sequence inserted into said β-lactamase gene.
    wherein said β-lactamase gene is linked to a β-lactamase promoter and a trp promoter located upstream from said β-lactamase promoter,
    wherein said trp promoter overrides said βlactamase promoter in effecting expression of said foreign DNA sequence.

2. The hybrid plasmid of claim 1 wherein said foreign DNA sequence encodes the surface antigen of hepatitis B virus.

3. The hybrid plasmid of claim 2 wherein the foreign DNA sequence is inserted into the PstI site of the β-lactamase gene.

4. The hybrid plasmid of claim 1 wherein the foreign DNA sequence is inserted into the PstI site of the β-lactamase gene.

5. A microorganism transformed by the plasmid of claim 1.

6. The microorganism of claim 5 which is *E. coli*.

* * * * *